United States Patent [19]
Maganas et al.

[11] Patent Number: 5,676,070
[45] Date of Patent: Oct. 14, 1997

[54] APPARATUS AND METHODS FOR CATALYTIC, LOW TEMPERATURE DEGRADATION OF MEDICAL WASTE AND OTHER ORGANIC MATERIALS

[76] Inventors: Thomas C. Maganas, 1200 Ardmore, Manhattan Beach, Calif. 90266; Alan L. Harrington, 1824 Scenic Dr., Modesto, Calif. 95355

[21] Appl. No.: 659,113

[22] Filed: Jun. 3, 1996

Related U.S. Application Data

[63] Continuation of Ser. No. 365,468, Dec. 27, 1994, abandoned.

[51] Int. Cl.$^6$ ........................................................ F23G 5/00
[52] U.S. Cl. .............................. 110/245; 110/254; 110/194
[58] Field of Search ............................ 110/244, 245, 110/248, 254, 256, 346, 194

[56] References Cited

U.S. PATENT DOCUMENTS

| | | | |
|---|---|---|---|
| 3,841,242 | 10/1974 | Sigg | 110/257 |
| 4,052,173 | 10/1977 | Schultz | 48/202 |
| 4,308,806 | 1/1982 | Vemura et al. | 110/346 |
| 4,497,637 | 2/1985 | Purdy et al. | 48/111 |
| 4,623,400 | 11/1986 | Japka et al. | 148/6.35 |
| 4,886,001 | 12/1989 | Chang et al. | 110/346 |
| 4,974,531 | 12/1990 | Korenberg | 110/245 |
| 4,977,840 | 12/1990 | Summers | 110/346 |
| 4,991,521 | 2/1991 | Green et al. | 110/245 |
| 5,010,830 | 4/1991 | Asuka et al. | 110/245 |
| 5,181,795 | 1/1993 | Circeo, Jr. et al. | 405/128 |
| 5,335,609 | 8/1994 | Nelson et al. | 110/346 |
| 5,347,936 | 9/1994 | Thorhuus | 110/245 |

FOREIGN PATENT DOCUMENTS

| | | |
|---|---|---|
| 0176123 A1 | 4/1986 | European Pat. Off. . |
| 2687765 | 8/1993 | France ............ 110/194 |

OTHER PUBLICATIONS

Guedes De Carvalho et al., *Mass Transfer Around Carbon Particles Burning In Fluidised Beds*, 63–70, Trans. IChemE., vol. 69, Part A (1991).

Molerus, O., *Heat Transfer In Gas Fluidized Beds. Part 1*, 1–14, Powder Technology, 70 (1992).

Shafey et al., *Experimental Study On A Bench-Scale, Batch-Type Fluidized-Bed Combustor For Energy Production From Waste-Derived Fuels*, 331–338, Energy, vol. 17, No. 4 (1992).

Kuipers et al., *A Numerical Model Of Gas-Fluidized Beds*, 1913–1924, Chemical Engineering Science, vol. 47, No. 8 (1992).

Jean et al., *Fluidization Behavior Of Polymeric Particles In Gas-Solid Fluidized Beds*, 325–335, Chemical Engineering Science, vol. 47, No. 2 (1992).

Homsy et al., *Report Of A Symposium On Mechanics Of Fluidized Beds*, 477–495, J. Fluid Mech., vol. 236 (1992).

Conversion Technology, Inc., *Source Test Report: Fluid Bed Stripping For Particulates, Metals, POCHS*, (1991).

Seghers Engineering, *Segers Zerofuel: A Concept For Autothermal Sludge Incineration* (1992).

Agarwal, Kedar, *Pyrolysis of Polymer Waste*, pp. 232–245, Society of Plastic Engineers, "Plastics Recycling: Technology Charts the Course" (Nov. 4, 1994).

*Primary Examiner*—Thomas E. Denion
*Attorney, Agent, or Firm*—Workman, Nydegger & Seeley

[57] ABSTRACT

Methods and Systems for catalyzing the oxidative destruction of animal tissues, particularly medical waste and animal and human corpses. A reaction chamber containing a fluidizable media is maintained at a temperature sufficient to cause the fluidized media, typically silica sand, silica gel, or alumina, to become highly reactive in the presence of moisture. Typically the reaction chamber is maintained at a temperature in a range from about 400° C. to about 500° C. The methods and systems quickly and efficiently destroy medical waste and a variety of other animal tissues such as corpses. The apparatus can be small to fit into small rooms or large to serve institutional needs. It replaces incineration, autoclaving, plasma formation, and the like as the preferred method for effectively disinfecting and destroying medical wastes and corpses.

18 Claims, 2 Drawing Sheets

APPARATUS AND METHODS FOR CATALYTIC, LOW TEMPERATURE DEGRADATION OF MEDICAL WASTE AND OTHER ORGANIC MATERIALS

This is a request for filing a file-wrapper-continuation application under 37 C.F.R. § 1.62, of prior application Ser. No. 08/365,468, filed on Dec. 27, 1994, now abandoned for APPARATUS AND METHODS FOR CATALYTIC, LOW TEMPERATURE DEGRADATION OF MEDICAL WASTE AND OTHER ORGANIC MATERIALS by the following inventors: Tom Maganas and Alan Harrington.

BACKGROUND OF THE INVENTION

1. Field of the Invention

The present invention relates to improved methods and systems for the degradation of organic waste materials, particularly medical wastes and other undesirable and potentially dangerous or infective animal tissues. More particularly, the invention provides methods and systems for destroying, by oxidatively breaking down into a gaseous state, animal tissues, including pathogen- and cell-containing biological tissues, using a reaction chamber containing a fluidizable catalytic reactive media, such as silica and/or alumina, together with reaction enhancing gases. The method and apparatus provide a quick, single-step, relatively low cost, low temperature method for not only disinfecting but completely destroying once-living tissue, including all viruses, bacteria, or other pathogenic agents residing therein, associated with medical waste or the disposal of, e.g., animal or human corpses.

2. Review of the Relevant Technology

The disposal of medical waste in a manner that will not release dangerous pathogenic or disease-causing agents into the environment has always been a relatively expensive and difficult task. This is because it is necessary to first kill all pathogenic or potentially pathogenic agents, and then completely destroy the tissue to prevent further rotting and decay of the tissue. Otherwise, the tissue can provide a haven where later-introduced foreign pathogenic agents can thrive. For instance, it is inadequate to simply sterilize once-living human tissue and then dispose of it like ordinary refuse where it will be exposed to bacteria or other natural bio-degradation agents. In the process of natural degradation, human infection-causing agents can find their way to the discarded human tissue, where they can thrive and then reinfect others. It is therefore necessary to not only disinfect but completely destroy this human pathogen "food" to prevent the chance that diseases might be spread in the future as a result of the improper disposal of the human tissue.

One method for destroying medical waste in the past has been incineration. While this appears to both sterilize and destroy the medical waste, the process has proved inadequate as a means to ensure total destruction of all pathogenic agents, including viruses. This is because of the inability to achieve complete combustion or destruction of all viruses or other pathogenic agents before they find their way out the smoke stack, or flue, of the incinerator. It has been found that "cold pockets" can exist within the incineration chamber and flue in which viruses or other pathogens can escape unharmed from the incineration process. This is due to the inter-relationship between the tremendous updrafts present in incinerator flues and the possibility that the chemical reaction dynamics necessary to completely destroy all viruses, bacteria, or other pathogens are inadequate to ensure complete destruction of the viruses or bacteria before they are carried up through the flue by the fast moving flue gases.

It is known that incinerators, by their very nature, expel hot gases through the flue. Huge volumes of air, in addition to the gases and solids that combust in the presence of oxygen to form mainly carbon dioxide and water (assuming complete combustion), are sucked up through the incinerator flue at high speed. Gases rise from the bottom of the incinerator to the top of the flue exit hole in a matter of seconds. Moreover, no matter how hot the incinerator is within the actual combustion chamber, the rising flue gases are generally much cooler, relatively speaking.

It is also the case that all chemical reactions, including the evaporation of water and combustion of organic materials in the presence of oxygen at high temperature, do not occur instantaneously. Instead, they follow fairly well-defined patterns or reaction dynamics from the beginning to the end of the reaction process. One theory for the known ability of viruses and other pathogens to escape unharmed from the incinerator flue is the ability of the hot updraft gases to lift small, lightweight particulate masses that may include or contain viruses or other pathogens at high speed through and out the flue before enough time has elapsed to ensure proper combustion of the virus or other pathogen. This phenomenon might be aided by the presence of water within most medical wastes, which can provide a localized cooling effect in the vicinity of any uplifted particles that are moist. The evaporation of water can, in theory, provide an evaporative cooling effect on a microscopic level because of the relatively high amount of enthalpy required to vaporize water. Perhaps pockets of evaporating water within the medical wastes can provide cool channels or zones that are quickly lifted up and then expelled through the flue by the aforementioned under high speed flue gases.

Moreover, simply making the incinerator hotter is ineffective to solve the problem of cold pockets. Any increase in the rate of incineration of the medical waste by the temperature increase is more than offset by the concomitant increase in the velocity of the updraft that can more quickly carry unburned viruses or other pathogens up and out the flue. With respect to other kinds of once living tissues, such as discarded animal or human corpses, the impending scarcity of available land for grave sites will severely inhibit the luxury of simply burying our dead in the future. In fact, many societies, both old and new, have customarily disposed of corpses in a manner that does not require the use of huge tracts of land. One such method is, of course, cremation. However, cremation, while generally effective, is analogous to the incineration method of destroying medical wastes and has each of its limitations, including the inability to achieve complete combustion of all inorganic materials, including viruses or other pathogenic agents.

Moreover, the environmental impact of the disposal of medical wastes or other once-living human or animal tissues should not be overlooked. Instead of incineration, some have attempted to first disinfect the infectious waste and then dispose of it in landfills. Besides the fact that our nation's landfills are in ever diminishing short supply, such medical wastes must be specially disposed of to prevent environmental contamination, at least in part because of the aforementioned tendency of dead human tissues, even previously sterilized tissue, to harbor disease-causing bacterial or other pathogenic agents. Moreover, auto-claving, a common method for sterilizing medical wastes, has also proven to not be completely reliable in ensuring the complete destruction of viruses or other pathogenic agents found in medical wastes because of the inability to evenly apply sufficient heat to ensure the complete destruction of the pathogenic agents Finally, because of the ever-increasing number of medical procedures and cures that are continuously being developed, the likelihood is that the amount of medical wastes that will need to be disposed of every year will increase indefinitely. Moreover, the ever-increasing amount of biotechnical research and development being performed in order to find new cures for human or animal diseases is responsible for the creation of dangerous disease-causing agents that, if accidentally released into the environment, could be catastrophic to the health of humans or animals. Hence, the need to efficiently and completely disinfect these and the aforementioned medical wastes has become acute and will continue to increase into the future.

A recently developed method for disinfecting and destroying toxic medical wastes and other organic materials is to destroy them in situ within a land disposal site using extreme temperatures. For example, U.S. Pat. No. 5,181,795 to Circeo, Jr. et al., teaches a method for destroying biological wastes by drilling a series of holes into which the organic waste is to be disposed, inserting a plasma arc torch in each hole to pyrolyze, remediate, and vitrify the waste materials, and then allowing the melted materials to cool down into essentially a chunk of glass. While of some interest, the method taught in Circeo, Jr. et al. is impractical for the destruction of either medical wastes or human corpses because it must be done remotely at a landfill site, which necessitates the transport of infectious wastes and corpses over potentially long distances before they can be destroyed. In addition, because the method involves the high temperature fusion of such wastes at plasma developing temperatures, the procedure is very costly. Moreover, Circeo, Jr. et al. refers to gases that are given off by pyrolysis, which gases must be burned in order to eliminate the potentially noxious fumes that may be emitted into the atmosphere. Finally, while the method reduces the mass of medical and other wastes, it does not eliminate the need to find new sites to perform the plasmation process, which sites are separate and apart from conventional landfill space, thereby exacerbating rather than reducing the problems associated with finding suitable waste disposal space.

In view of the foregoing, it would be a significant advancement in the art to provide methods and systems that would result in complete and reliable destruction of medical wastes and other once-living human or animal tissue.

It would be a further advancement in the art if such methods and systems resulted in the complete and reliable destruction of medical wastes and other once-living human or animal tissue in a simple, single step without polluting the environment.

It would be another advancement in the art if such methods and systems ensured the complete destruction of all viruses, bacteria, or other pathogenic agents that might be found in the medical waste or corpse being disposed of.

It would be an additional advancement in the art if such methods and systems completely and thoroughly destroyed the medical waste or other once-living human or animal tissue without the generation of noxious gases..

It would be an additional advancement in the art if such methods and systems completely and thoroughly destroyed the medical waste or other once-living human or animal tissue at relatively low temperatures compared to conventional incineration or plasma forming methods.

Finally, it would be a considerable advancement in the art to provide apparatus for carrying out such methods that were relatively small and portable and that could be stationed at a variety of locations within a hospital, research laboratory, or other situs where medical wastes or corpses need to be destroyed without the possibility that dangerous viruses or pathogens could be released into the environment, particularly at a hospital or laboratory where sterile conditions are especially vital, or through the transport of such wastes to available landfill sites.

Such methods, systems, and apparatus are disclosed and claimed herein.

SUMMARY AND OBJECTS OF THE INVENTION

The present invention relates to improved methods and systems for the complete and reliable destruction of medical wastes or once-living human or animal tissues. Such methods not only ensure the complete destruction of the actual physical or visible wastes or tissues, but also ensure the complete destruction of all viruses, bacterial, or other pathogenic agents that might be found in the medical wastes or tissues. Moreover, such destruction is carried out without the need for chemical sterilization, autoclaving at high temperature and pressure, high temperature incineration, plasma arcs, and the like. Instead, the present invention utilizes a reaction chamber containing a reactive catalytic media, such as silica, alumina, and the like, together with reaction enhancing gases, such as oxygen and water vapor.

Although the technology of providing a fluidizable medium in order to cause the pyrolysis or cracking of certain organic materials has been known, it was heretofore not known that a reaction chamber containing an appropriate fluidizable media could be used to completely and inexpensively destroy highly dangerous infectious wastes, while always ensuring complete and absolute sterilization of the waste and destruction of all pathogens. An example of a fluidized bed is found in European Patent Application Publication No. 0,176,123, filed Aug. 26, 1985, in the name of Geeroms (hereinafter "EU '123"), which discloses a "whirl bed" comprising a metal chamber, a fluidizable media such as silica, means for introducing heated gases through fluidizable media, and an afterburner for burning any gases that are formed by pyrolysis. The purpose for the whirl bed in EU '123 is to clean metal parts upon which paint, rubber, or other hard to remove substances have adhered. EU '123 appears to rely, however, on the combination of the abrasive action of the whirling sand media and a high enough temperature (preferably 650° C.) in order to effect the mechanical and pyrolytic removal of the adhered organic substances to clean the metal parts. EU '123 did not understand or teach that at lower temperatures and in the presence of abundant oxygen and adequate moisture that organic materials, such as medical wastes or corpses, could be catalytically digested and completely destroyed through oxidative destruction. In fact, EU '123 teaches that combustible gases such as methane gas rather than oxygen or water vapor should be passed through the whirl bed during operation.

In contrast to EU '123 and others who have used fluidized bed technology, the inventors of the present technology have discovered that what are believed to be an abundance of very reactive hydroxyl radicals and other reactive hydrogen oxide species (and possibly other oxide species) are generated through the interaction of water vapor and the otherwise apparently inert silica or alumina particles of the fluidizable media at temperatures of at least about 400° C. Although silica sand is largely comprised of monolithic crystals of silicon dioxide, the surface of silicon dioxide particles in a fluidized state can react at elevated temperatures with water vapor to create highly reactive fluidized silica particles. It is known that at elevated temperatures silica will become hydrated in water to form silicic acid, which is empirically represented as $Si(OH)_4$, as well producing less stable intermediate moieties.

In the environment generated by the fluidized media, the reactive silica surface containing silicic acid or its intermediates appears to generate and emit highly reactive radicals or other reactive species that quickly oxidize any organic material coming in contact with, or even in the vicinity of, the media particle. Alumina also appears to generate very reactive oxidants under the same conditions. The exact mechanism of the oxidative breakdown of organic wastes, including medical wastes and corpses, is unknown at this time; however, a fluidized media in which adequate moisture is present and the temperature is in a range from about 400° C. to about 500° C. has been demonstrated to completely destroy an entire pig corpse in less than 45 minutes, leaving no bones, teeth, or any detectable solid residue other than nonoderiferous gases and traces of ash. Providing an oxygen-rich environment also seems to increase the oxidative breakdown of the organic wastes, although breakdown is also observed even in an oxygen-poor environment within the reaction chamber.

As a result of the newly discovered interaction between the fluidized media at the aforementioned temperatures in the presence of moisture to create a highly oxidative environment, and because it is desirable to promote as much oxidation as possible, it is not preferable to feed methane or other combustible gases into the fluidized media. To do so would tend to compete with the medical waste or corpse for the oxidants that are generated. Contrary to EU '123, instead of feeding methane gas through the fluidizable media, Applicants have found it preferably to simply feed heated air, preferably oxygen rich air, through the media. Oxygen would be expected to interact with and enhance the oxidative action of the oxidants that are generated by the fluidized media particles in the presence of water at elevated temperatures.

Because the fluidizable media is not merely a catalyst but is also a reactant to some extent, it would be expected that the fluidizable media would break down over time, or become "used up" as medical wastes are consumed. In fact, it appears that a measurable fraction of the fluidized media is broken down over time, although the amount is small in comparison to the molar equivalents of organic material being oxidatively consumed. Nevertheless, an advantage of the present invention is the exploitation of the highly reactive nature of the fluizable media instead of the enormous amounts of energy that are expended in producing a hot enough incinerator to effectively destroy the medical wastes by burning. This advantage is particularly apparent in light of the extremely low cost of fluidizable media such as silica or alumina, which are readily available, largely inert until exposed to the reactive conditions, and very inexpensive.

In the case where the medical or other organic waste generated appreciable amounts of halogen- or sulfur-containing vapors, it has been found advantageous to inject ammonia gas into the reaction chamber along with the heated air in order to react with and bind such waste gases.

A preferred apparatus for the catalytic destruction of medical wastes or corpses includes a reaction chamber, a corresponding volume of a fluidizable media, such as silica sand, silica gel, or alumina, means for fluidizing the media, means for maintaining the temperature of the reaction chamber to a desired temperature or temperature range, means for collecting any ash or other solids generated by the reaction process, and an means for exhausting the gases that are generated by the reaction process. The apparatus may optionally include means for introducing a variety of gases within the reaction chamber, such water vapor, oxygen, ammonia, etc. In a preferred embodiment, the means for fluidizing the media, maintaining the temperature at the desired level, and introducing oxygen rich gas into the reaction chamber all comprise means for introducing heated air into the reaction chamber at a preferred temperature and velocity. In many cases it will be unnecessary to further enrich the reaction chamber with water vapor in light of the fact that both medical wastes and corpses contain large amounts of water that are vaporized upon their being introduced into the reaction chamber.

If flammable gases are generated in appreciable amounts by the reaction chamber, it may be preferably to ignite such gases by means of an afterburner. The heat that is generated within the reaction chamber, as well as heat produced by the optional afterburner, can be used to maintain the desired temperature of the reaction chamber. The heat held within the exhaust gases can be recirculated by means of, e.g., a heat exchange or by simply recycling some or all of the gases through the reaction chamber. In the latter scenario, it might be preferable to enrich the burnt gases with oxygen before feeding them back into the reaction chamber. Because of the catalytic nature of the reaction process, a more thorough breakdown of the intermediate gases that might otherwise be present by conventional incineration is carried out, thereby greatly reducing or eliminating altogether in most cases the generation of noxious fumes.

Because of the nature of the reaction process, it is possible to greatly upscale or downscale the reaction apparatus size to accommodate a variety of uses. The reaction apparatus and chamber may be very large in order to serve large institutional needs such as a huge medical or research complex. Conversely, it may be very small and portable when only required to destroy a small but steady stream of medical wastes. The latter also provides for ease in moving and placement of the reaction apparatus in the most convenient location.

Because the medical waste is quickly and efficiently disinfected and destroyed by the inventive process, it greatly simplifies the heretofore significant problems associated with the disposal of medical wastes. It also provides a means for the complete disposal of animal or human corpses while generating no more ash than traditional cremation by incineration, which requires far more energy to carry out and which is known to generate noxious gases.

In view of the foregoing an object and feature of the present is to provide methods and systems that result in the complete and reliable destruction of medical wastes and other once-living human or animal tissue.

Another object and feature is to provide methods and systems that result in the complete and reliable destruction of medical wastes and other once-living human or animal tissue in a simple, single step without polluting the environment.

A further object and feature of the present invention is to provide methods and systems that ensure the complete destruction of all viruses, bacteria, or other pathogenic agents that might be found in the medical waste or corpse being disposed of.

Yet another object and feature is to provide methods and systems which completely and thoroughly destroy the medical waste or other once-living human or animal tissue without the generation of noxious gases.

Still and further object and feature of the present invention is to provide methods and systems that completely and thoroughly destroy the medical waste or other once-living human or animal tissue at relatively low temperatures compared to conventional incineration or plasma forming methods.

Finally, it is an object and feature of the present invention to provide apparatus for carrying out the foregoing methods that are relatively small and portable that could be stationed at a variety of locations within a hospital, research laboratory, or other situs where medical wastes or corpses need to be destroyed without the possibility that dangerous viruses or pathogens can be released into the environment, particularly at a hospital or laboratory where sterile conditions are especially vital, or through the transport of such wastes to available landfill sites.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity in detail to the use of the accompanying drawings in which.

DETAILED DESCRIPTION OF THE PREFERRED EMBODIMENTS

The present invention relates to improved methods and systems for disinfecting and completely destroying organic waste materials, particularly medical wastes and corpses. Such methods and systems ensure the complete destruction of both the medical waste or corpse, as well as all pathogenic agents, such as viruses and bacteria that may reside therein. The sterilization process is carried out without the need for chemical disinfectants, autoclaving at high temperature and pressure, high temperature incineration, plasma arcs, and the like. Instead, the present invention utilizes the ability of a fluidizable media such as silica or alumina to generate highly reactive oxidants in the presence of moisture within a preferred temperature range to carry out the simple but complete destruction and disinfection of medical wastes and corpses under relative mild conditions. Such destruction is carried out in a single chamber, at a relatively constant temperature, and in a one-step process. This allows for the reliable destruction of organic wastes without the attendant problems of high temperature formation of $NO_x$ and $SO_x$ typical in high temperature combustion.

The terms "degrade" or "degradation", as used in the specification and the appended claims, refer to the breakdown of larger organic molecules within the organic waste material into smaller organic molecules, mainly through the oxidative cleavage of carbon-carbon bonds. These terms shall also refer to the cleavage of any other molecular bonds during the process of gasifying and oxidizing. It also includes the complete oxidation of such gases into mainly carbon dioxide and water. Degradation of medical wastes does, however, generate a small amount of ash, which can be collected for sentimental reasons or appropriately discarded.

The terms "medical waste" or "medical wastes", as used in the specification and the appended claims, shall refer to all human tissues that are removed from, or which otherwise have their origin in, the human body. These terms include, but are not limited to, tissues, organs, skin, tumors, bones, cartilage, connective tissue, blood vessels, and the like that are removed from the human body as a result of, e.g., surgery or other means for excision of such from the body. The term "medical waste" shall also include all similar tissues removed from animals, such as pets, cattle, zoo animals, and all other domestic and nondomestic animals, both warm and cold-blooded.

The terms "corpse", "animal corpse", and "human corpse", as used in the specification and the appended claims, shall have their ordinarily understood meanings and shall refer, for example, to any animal or human body that has expired, and which can be advantageously eliminated by the methods and systems described and claimed herein. The term "human corpse" is a subset of "animal corpse", which shall refer to the corpse of any living thing.

The terms "animal tissue", "once-living tissue", or "human tissue", as used in the speicification and the appended claims, shall refer to any animal or human tissue, including medical wastes or corpses as defined above. The term "human tissue" is a subset of the terms "animal tissue" or "once-living tissue". Of course, while in some cases the medical waste or corpse being disposed of might be considered to be "living" in some sense of the word, such shall be considered to be within the definition of "once-living" if it is nevertheless useless or otherwise desirable of being discarded.

The term "portable", as used in the specification and the appended claims, shall refer to the ability of the apparatus used to carry out the methods of the present invention, as embodied in certain embodiments, to be capable of being moved throughout a building or medical or research facility where needed. This movement of the apparatus might be by simply carrying the apparatus, wheeling the apparatus by means of a supporting stand equipped with rollers or wheels, or moving the apparatus by means of moving equipment (e.g., a forklift or small crane), the important feature being that a portable apparatus is not primarily a fixture as the term is commonly understood.

Figure 1:
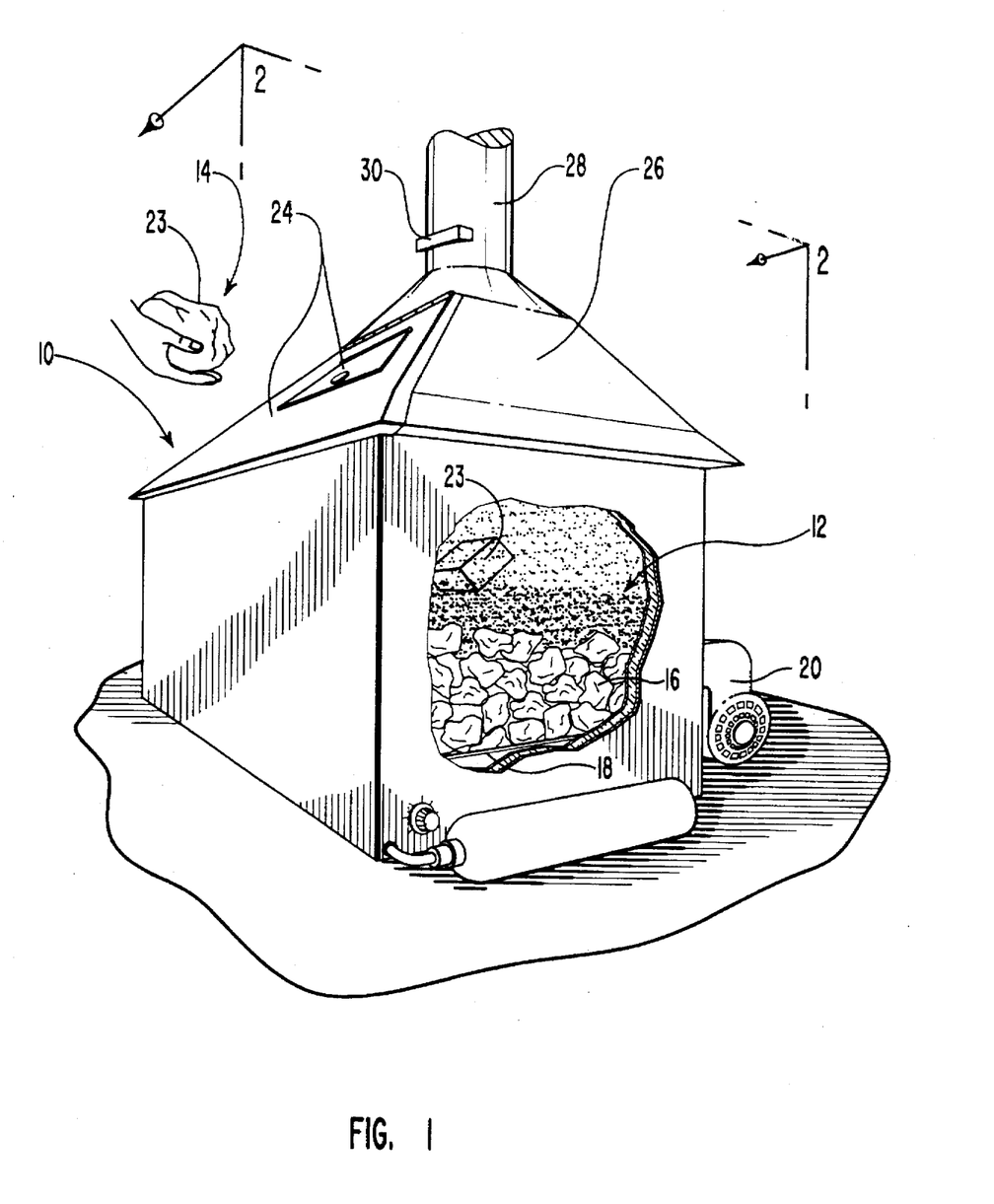
FIG. 1 is a perspective view of a preferred reaction apparatus into which a packet of medical waste is being inserted.

A preferred apparatus for carrying out the preferred method of destroying medical waste or corpses is illustrated in FIG. 1. The reaction apparatus 10 of FIG. 1 includes a catalytic reaction chamber 12 containing a fluidizable media 14 capable of catalyzing the oxidative degradation of medical wastes or corpses. The reaction chamber 12 is generally sealed except for where air is introduced into the bottom of the reaction chamber to fluidize the media 14, the medical waste or corpses is introduced, and at the top of the reaction chamber where exhaust gases are removed.

Figure 2:
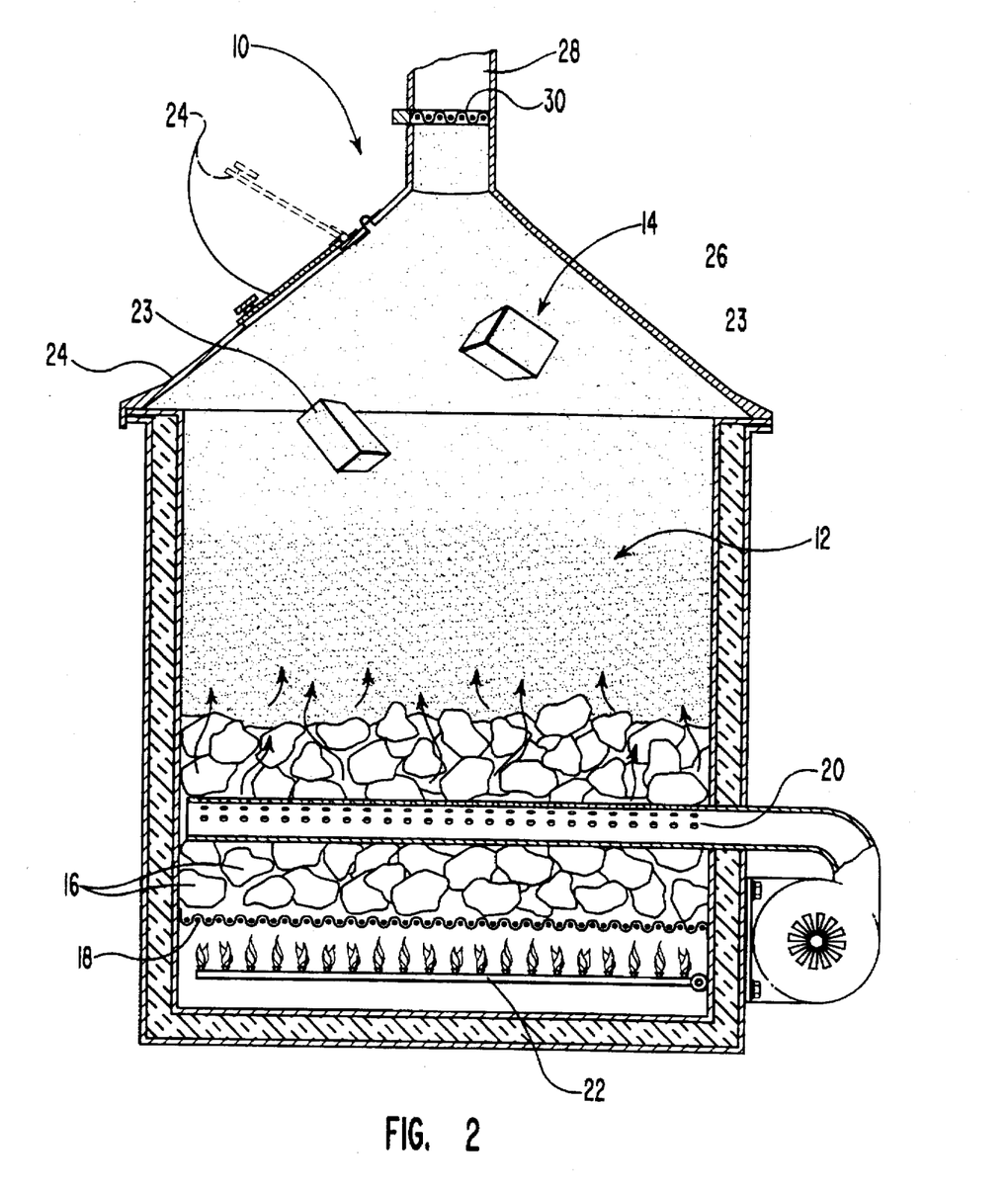
FIG. 2 is a cross-sectional view of the reaction apparatus of FIG. 1.

The fluidizable media preferably comprises sand-like particles of a material such as silica sand, silica gel, alumina, and the like. Silica sand, silica gel, alumina, and mixtures thereof are preferred media because of their low cost. The fluidizable media 14 preferably sits atop a bed of nonfluidizable pebbles or rocks 16, which are included mainly for the more efficient transfer of heat and moving air throughout the fluidizable media 14 and reaction chamber 12. The rocks 16 sit atop a support plate 18, which is sealed so that air introduced through the rocks 16 will travel upward through the fluidizable media and not downward. The support plate 18 preferably comprises a heat conductive metal to ensure effective transfer of heat in the case where the heat used to regulate the temperature of the reaction chamber 12 and the fluidizable media 14 lies beneath the surface of the reaction chamber.

Because it is necessary to fluidize, or elevate with heated air, the fluidizable media 14, the reaction apparatus 10 is equipped with means for fluidizing the media 14. A preferred fluidizing means includes air jets 20, which are preferably located within the rocks 16 to ensure a more disperse air flow through the fluidizable media 14. However, the air jets 20 can be situated directly within the fluidizable media 14, typically in embodiments where rocks 16 are not employed. The air that is introduced by means of air jets 20 may be preheated to approximately the desired temperature of the reaction chamber 12, or it may become heated by means of heat that radiates through the metal support plate 18 and rocks 16. In the latter case, it will be necessary to provide means for heating the support plate 18, which may comprise burners 22, or an electric resistive heater built therein. Of course, in the case where an electric heater is used it will be more efficient to simply situate the heater within the reaction chamber 12.

The air that is introduced into the reaction chamber by air jets 20 may be preheated by a number of means, including electric heating means or radiative heating means heated by a fuel such as natural gas, fuel oil, or coal, where it is desired to pass pure air through the reaction chamber. However, it may be more economical to simply burn natural gas directly into the air being introduced in the reaction chamber 12. Because the natural gas produces mainly water and carbon dioxide, the combustion gases should not inhibit the reaction process within the reaction chamber 12. In fact, the generation of water vapor would be expected to enhance the reactivity of the fluidized media 14. Because the combustion gases are preferably blended with air in order to provide the proper temperature conditions, the air that is introduced into the reaction chamber 12 will include adequate oxygen in most cases. However, it will be possible to enrich the air with pure oxygen if desired to increase the reactivity within the reaction chamber 12.

The air that is introduced through air jets 20 should have sufficient velocity and pressure to cause the fluidizable media 14 to become "fluidized" as the term is understood by one of ordinary skill in the art, but not so great so as to churn the media 14 too vigorously or carry gases from the reaction chamber 12 too rapidly. In order to ensure the best and most efficient reaction, it is preferably to blow just enough air to effect adequate fluidization of the media and no more. The less air that actually passes through the reaction chamber, while maintaining adequate fluidization will use less energy and require less enrichment gases that are passed through the reaction chamber 12.

The preferred apparatus is equipped with means for introducing medical wastes for corpses within the reaction chamber 12. As shown in FIG. 1, medical wastes can be introduced into the reaction chamber 12 in the form of packets 23 through door 24. The door 24 should be capable of quickly opening to receive the waste packet and then closing in order to keep the heat within the reaction chamber 12. In an alternative embodiment, a set of double doors 24 may be employed to better maintain heat within the reaction chamber 12, with a first door 24 opening to allow the introduction of a medical waste packet within a prechamber, after which a second door 24 would open up into the reaction chamber proper.

In the case where very large packets of medical waste or corpses are introduced into the chamber, it might be preferable to open the reaction through a lid 26 covering the top of the reaction chamber. In that case it may be necessary to restore the temperature within the reaction chamber 12 by temporarily increasing the temperature of the air that is introduced into the reaction chamber or by turning up the heat of burners 22.

Connected to the lid 26 at the top of the reaction chamber 12 is exhaust conduit 28, which carries the waste gases to the appropriate location for emission into the outside air. In cases where the waste gases comprise appreciable amounts of combustible gases it may be desirable to further combust them by means of an afterburner. Heat within the waste gases can be recycled back into the reaction chamber by any appropriate method known to those of ordinary skill in the art, such as by heat exchange, to heat up the air introduced into the reaction chamber, or by simply recirculating the gases back into the reaction chamber 12 to ensure complete breakdown of all organic gases. This may be one means of ensuring the complete destruction of any viruses or pathogenic agents, although it is believed that none can escape the reaction chamber during the waste destruction process. Because there are no cold pockets within the fluidized media 12, the medical waste, viruses, bacteria, and all are at least completely disinfected if not fully broken down into gases. Viruses and bacteria, even if not vaporized immediately within the reaction chamber 12, are nevertheless effectively killed by the being exposed to heat in a temperature range from about 400° C. and about 500° C.

Within exhause conduit 28 may be one or more optional filters 30, which are used to remove all fly ash or other airborne particles generated by the inventive reaction processes. In the case where, for sentimental reasons, it may be desired to collect the ashes from, e.g., the destruction of a corpse, the filters 30 provide such a means, particularly if equipped with shaking and collecting means that can be actuated between each batch for reliable collection of particular ashes that are generated so as to not commingle ashes from one corpse to another. If sentimental reasons are of no concern, the ashes can be discarded or used for, e.g., fertilizer. A preferred filter is a ceramic filter.

In a preferred method for destroying both medical waste and animal or human corpses, the temperature within reaction chamber 12 is maintained in a range from about 400° C. to about 500° C., more preferably in a range from about 420° C. to about 480° C. Below the outer range the reaction is greatly inhibited. Above the outer range the excess heat is unnecessary and, therefore, inefficient. Through mechanisms that are not entirely understood, the inventors have found that medical wastes, corposes, and other organic wastes are efficiently digested and oxidized by means of the fluidized media if there is an adequate amount of moisture within the reaction chamber 12 to cause the generation of what are believed to be reactive hydroxyl radicals, hydrogen oxides, oxides, or other highly oxidative agents. Because of the oxidative nature of the reaction process, it is also preferable to ensure that there is abundant oxygen within the air being introduced into the reaction chamber. It is believed that it is the generation of highly reactive hydroxyls and other moieties that is responsible for the observed destruction of medical wastes and corpses.

The packets of medical waste may be encapsulated within any appropriate encapsulation material capable of being catalytically oxidized in the same manner as the medical waste within the reaction chamber 12. These include paper, thin plastic bags, and the like.

In some cases it might be desirable to adjust the composition of the atmosphere within the reaction chamber 12. For example, it may be necessary to increase the amount of oxygen within the reaction chamber 12 by intermittently injecting oxygen within the reaction chamber 10 in order to effect oxidation of a particular medical waste packet. In addition, it may be necessary to introduce more moisture in the form of water vapor within the reaction chamber 12 in order to more fully activate the fluidized media particles. Because most medical wastes and corpses will naturally contain abundant water, it will usually be necessary to supplemental this water with additional moisture. Nevertheless, it may be desirable to do so before any wastes are first introduced into the reaction chamber in order to preactivate the fluidizable media particles 14. Finally, it may be desirable to introduce other reactive gases within the chamber such as ammonia gas, which can be added to precipitate halogens such as chloride or fluoride or sulfurous compounds that are generated during the degradation process. Any of these gases may be introduced together with the air by means of air jets 20.

EXAMPLE

In order to demonstrate that a fluidizable media within a reaction chamber would work to destroy a wide variety of once-living tissues, including medical wastes and corpses, a piglet corpse weighing about 35–40 lbs. was placed within a rection chamber containing silica sand as the fluidizable media. The reaction chamber was adapted from a commercially available fluidized bed manufactured by Dinamec, which is located in Belgium. The temperature was held to within a range from about 420°–425° C. Because the reaction chamber was not visible from the outside, it was not possible to visually detect how fast the piglet corpse was digested and destroyed. However, after 45 minutes, the reaction chamber was opened up and inspected. Nothing remained of the piglet corpse: there were no bones, no teeth, no tissues that could be detected, which proved that the reaction chamber under the above stated conditions became highly reactive and able to completely destroy the entire piglet corpse. This is especially evident since the reaction temperature was far below the ignition temperature required to burn a corpse.

In conclusion, the above-identified methods provide a simple and reliable way to ensure the complete destruction of pathogen-containing medical wastes or human or animal corpses using a reaction chamber that is relatively inexpensive, small, and portable, particularly in comparison to incinerators, which comprise huge structures that must be built separately from the hospital or research facilities that they might serve. For example, a relatively small reaction chamber measuring six feet long, three feet wide, and three feet tall can destroy about 250 pounds of medical waste per hour, which greatly exceeds the needs of most individual hospitals or research facilities. The relatively low energy requirements of the reaction chamber can be met by conventional natural gas conduits found in most buildings, bottled gaseous fuels, such as propane or butane, or liquified fuels, such as gasoline, kerosene, diesel, or fuel oils.

Of course, the dimensions of the reaction chamber can be altered for any particular need. The reactor may be reduced in size to fit into smaller areas where only minor amounts of medical wastes are generated. Conversely, the reactor may be increased in size in order to serve a very large institution. Of course, while having many incinerators within different wings of a large hospital would be entirely impractical (not to mention impossible), having many small reaction chambers throughout a hospital would be quite feasible and, in fact, might actually be desirable for convenience. In addition, having a conveniently located reaction chamber could greatly cut down the time between when the medical waste is first generated and when it is actually destroyed. The potential for dangerous disease-causing agents to escape into the environment is greatly reduced if the medical waste can be more quickly and efficiently destroyed. The present invention dearly serves this valuable function. Moreover, a conveniently located reaction chamber obviates the need to transport the toxic medical wastes to more remotely located disposal sites. This cuts down the handling time and costs since the waste must normally be treated very cautiously and delicately to prevent the escape of pathogens into the environment.

Alternatively, the reaction chamber might be appropriately proportioned to effect the oxidative destruction of human or animal corpses. In many countries throughout the world, particularly those that are densely populated or which otherwise do not share the tradition of interring bodies within the earth, the present invention provides a cleaner, more efficient method for the cremation of human corpses. The destruction of animal corpses by the methods and systems of the present invention would be advantageous in, e.g., research laboratories or slaughter houses. In the event that the ash remains of a human corpse are desired for sentimental reasons, the reaction chamber can be provided with screens or sieves for the recovery of the ashes. Where sentimental concerns do not play a role, the ash recovered by such means can be disposed of or used for, e.g., fertilizer.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for catalytically degrading animal tissue or medical waste comprising the steps of:

suspending a media within a reaction chamber, said media including individual particles selected from the group consisting of silica, alumina, and mixtures thereof that are heated and maintained at a temperature of less than about 480° C. and exposed to moisture such that the media particles are catalytically reactive; and introducing the animal tissue or medical waste into the reaction chamber in order that the catalytically reactive media particles contact or come into close proximity to the animal tissue or medical waste and thereby catalytically degrade the animal tissue or medical waste within the reaction chamber at a temperature lower than about 480° C.

2. A method for catalytically degrading animal tissue or medical waste as defined in claim 1, wherein the animal tissue is catalytically oxidized in less than about 1 hour after first being introduced into the reaction chamber.

3. A method for catalytically degrading animal tissue or medical waste as defined in claim 1, wherein the animal tissue is catalytically oxidized in less than about 30 minutes after first being introduced into the reaction chamber.

4. A method for catalytically degrading animal tissue or medical waste as defined in claim 1, further including the step of introducing additional moisture into the reaction chamber in order to maintain the media particles catalytically reactive.

5. A method for catalytically degrading animal tissue or medical waste as defined in claim 1, further including the step of introducing additional oxygen into the reaction chamber in order to maintain the oxygen at a concentration greater than oxygen found in atmospheric conditions.

6. A method for catalytically degrading animal tissue or medical waste as defined in claim 1, further including the step of introducing ammonia into the reaction chamber in order to scavenge air-borne pollutants.

7. A method for catalytically degrading animal tissue or medical waste as defined in claim 1, wherein the suspended media comprises silica sand.

8. A method for catalytically degrading medical waste or animal corpses comprising the steps of:

suspending a media within a reaction chamber, said media including individual particles selected from the group consisting of silica, alumina, and mixtures thereof that are heated to a temperature in a range from about 400° C. to about 500° C. and exposed to moisture such that the media particles are catalytically reactive; and introducing the medical waste or animal corpse into the reaction chamber in order that the catalytically reactive media particles contact or come into close proximity to the medical waste or animal corpse and thereby catalytically degrade the medical waste or animal corpse within the reaction chamber.

9. A system for catalytically degrading medical waste or animal tissues comprising:

a single reaction chamber;

a suspended media within the single reaction chamber, the media including individual particles selected from the group consisting of silica, alumina, and mixtures thereof that become catalytically reactive and capable of catalyzing the oxidative degradation of medical waste or animal tissues exposed to the catalytically reactive media at a temperature lower than about 480° C.;

means for suspending the media particles, said suspending means disposed at least in part within the single reaction chamber and communicating with the media;

means for heating the media particles to a temperature up to about 480° C. in order for the media particles to become catalytically reactive, said heating means maintaining the media particles at a temperature less than about 480° C.;

means for exposing the individual media particles to moisture in order for the media particles to become catalytically reactive;

means for introducing the medical waste or animal corpse within the single reaction chamber in order that the catalytically reactive media particles contact or come into close proximity to the medical waste or animal tissues; and means for venting the combustion gases from the single reaction chamber.

10. A system for catalytically degrading medical waste or animal tissue as defined in claim 9, wherein the means for heating the media are located beneath the reaction chamber.

11. A system for catalytically degrading medical waste or animal tissue as defined in claim 9, wherein the means for heating the media include preheating air used to suspend the media.

12. A system for catalytically destroying medical waste or animal tissues as defined in claim 9, wherein the system is portable.

13. A system for catalytically destroying medical waste or animal tissues as defined in claim 9, wherein the means for heating the media particles maintain the media particles at a temperature in a range from about 400° C. to about 500° C.

14. A system for catalytically destroying medical waste or animal tissues as defined in claim 9, wherein the means for heating the media particles maintain the media particles at a temperature in a range from about 420° C. to about 480° C.

15. A system for catalytically destroying medical waste or animal tissues as defined in claim 9, wherein the suspended media comprises silica sand.

16. A system for catalytically destroying medical waste or animal tissues as defined in claim 9, wherein the means for suspending the media particles comprise air jets at least partially disposed within the single reaction chamber.

17. A system for catalytically destroying medical waste or animal tissues as defined in claim 9, further including means for introducing a desired gas into the single reaction chamber.

18. A system for catalytically degrading medical waste or animal tissues as defined in claim 17, wherein the means for introducing a desired gas into the single reaction chamber comprise air jets used to suspend the media.

* * * * *

UNITED STATES PATENT AND TRADEMARK OFFICE
CERTIFICATE OF CORRECTION

PATENT NO. : 5,676,070

DATED : October 14, 1997

INVENTOR(S) : Per Just Andersen; Simon K. Hodson

It is certified that error appears in the above-identified patent and that said Letters Patent are hereby corrected as shown below:

Col. 2, line 64, after "Moreover," change "auto-claving" to --autoclaving--

Col. 3, line 60, after "noxious" change "gases.." to --gases.--

Col. 5, line 6, after "as" change "Si(OH$_4$" to --Si(OH)$_4$

Col. 5, line 36, after "it" change "preferably" to --preferable--

Col. 6, line 4, after "and" delete "an"

Col. 6, line 18, after "be" change "preferably" to --preferable--

Col. 8, line 30, after "the" change "speicification" to --specification--

Col. 9, line 51, after "to" change "chum" to --churn--

Col. 9, line 54, after "is" change "preferably" to --preferable--

UNITED STATES PATENT AND TRADEMARK OFFICE
CERTIFICATE OF CORRECTION

PATENT NO. : 5,676,070

DATED : October 14, 1997

INVENTOR(S) : Per Just Andersen; Simon K. Hodson

It is certified that error appears in the above-identified patent and that said Letters Patent is hereby corrected as shown below:

Col. 11, line 17, before "this" change "supplemental" to --supplement--

Col. 12, line 15, after "invention" change "dearly" to --clearly--

Signed and Sealed this

Fifth Day of May, 1998

Attest:

BRUCE LEHMAN

*Attesting Officer*  Commissioner of Patents and Trademarks